United States Patent [19]

Wada

[11] 4,162,851
[45] Jul. 31, 1979

[54] SIMULTANEOUS PHOTOMETERING METHOD AND ASSEMBLY FOR MULTI-DIMENSIONAL MEASUREMENTS CONCERNING BIOLOGICALLY RELATED MATERIALS

[76] Inventor: Akiyoshi Wada, 11-4, Akasaka 8-chome, Minato-ku, Tokyo, Japan

[21] Appl. No.: 891,366

[22] Filed: Mar. 29, 1978

[51] Int. Cl.² .......................................... G01N 21/00
[52] U.S. Cl. ...................................... 356/73; 356/327
[58] Field of Search ................. 356/73, 318, 326, 327, 356/366, 367, 85, 96, 97, 115, 116

[56] References Cited

U.S. PATENT DOCUMENTS 3,390,605  7/1968  Nagamura .............................. 356/73

Primary Examiner—Vincent P. McGraw
Attorney, Agent, or Firm—Griffin, Branigan and Butler

[57] ABSTRACT

A method and apparatus for producing multi-dimensional measurements of biologically related materials involves radiating samples of the materials with left and right alternating circular polarizations of selected wavelengths. Both light transmissions through the samples and fluorescent light generated by the samples are detected. D.C. components of the transmitted light is used to determine light absorbency and A.C. components and D.C. components are used to determine circular dichroism. The data is displayed in manners to correlate with one another and with time. In this respect, three dimensional plots of a spectrum over a period of time can be obtained.

3 Claims, 4 Drawing Figures

SIMULTANEOUS PHOTOMETERING METHOD AND ASSEMBLY FOR MULTI-DIMENSIONAL MEASUREMENTS CONCERNING BIOLOGICALLY RELATED MATERIALS

BACKGROUND

This invention relates to a method and assembly for simultaneously measuring a plurality of characteristics of biologically related materials over a short period.

Biological materials, particularly biological high molecules such as protein, enzyme and others have complicated structures and reactivities. Various methods have been proposed for measuring their structure and reactivities both qualitatively and quantitatively.

To cite examples of spectrophotometering spectrum that are used for such measurements, there are absorption spectrum relating to primary structures of the materials as well as fluorescence spectrum, circular polarization dichroism spectrum and Raman spectrum relating to secondary structures. It is also known to obtain many types of information concerning the nature (structures and reactivities) of materials by varying the measuring conditions of temperature, solution concentration, pH value and others.

It cannot be said that general information relating to the structure and reactivity of a material can be secured by merely collecting results of individual analytical measurements obtained, because it is virtually impossible to gather a number of physically identified samples from a sample under the same conditions.

In addition, there are many cases where measuring samples from biological high molecules or biologically synthesized high molecules comprise multicomponent systems having both complicated chemical reactions and living activities. Such samples easily vary rapidly with given conditions and time. It is, therefore, essential for measurements concerning biological materials to be taken simultaneously and, at least during a short period.

This invention relates to a method and assembly for taking multi-dimensional and simultaneous measurements concerning biological materials to meet said requirement.

The simultaneous taking of various measurements for samples according to this invention advantageously contributes to shortening of measuring periods, but it is of more essential significance that serious correlations can be found from the data of various categories, so that progress to medical diagnosis (particularly clinical examination) and examination of other living bodies can be expected.

A purpose of this invention is to provide a method and assembly for simultaneously taking photometering and multi-dimensional measurements concerning biological materials. The invention is characterized in that selected wavelength lights are radiated onto samples as periodically alternating circular polarizations. Some transmissions through said samples are recognized to measure the circular dichroism and absorbency of said samples over a period of time and to also detect the strength of fluorescences which the samples are excited by said radiation to generate. This allows the invention to indicate and record the circular dichroism, absorbency and strength in correlative manners.

DESCRIPTION OF THE PREFERRED EMBODIMENT

Figure 1:
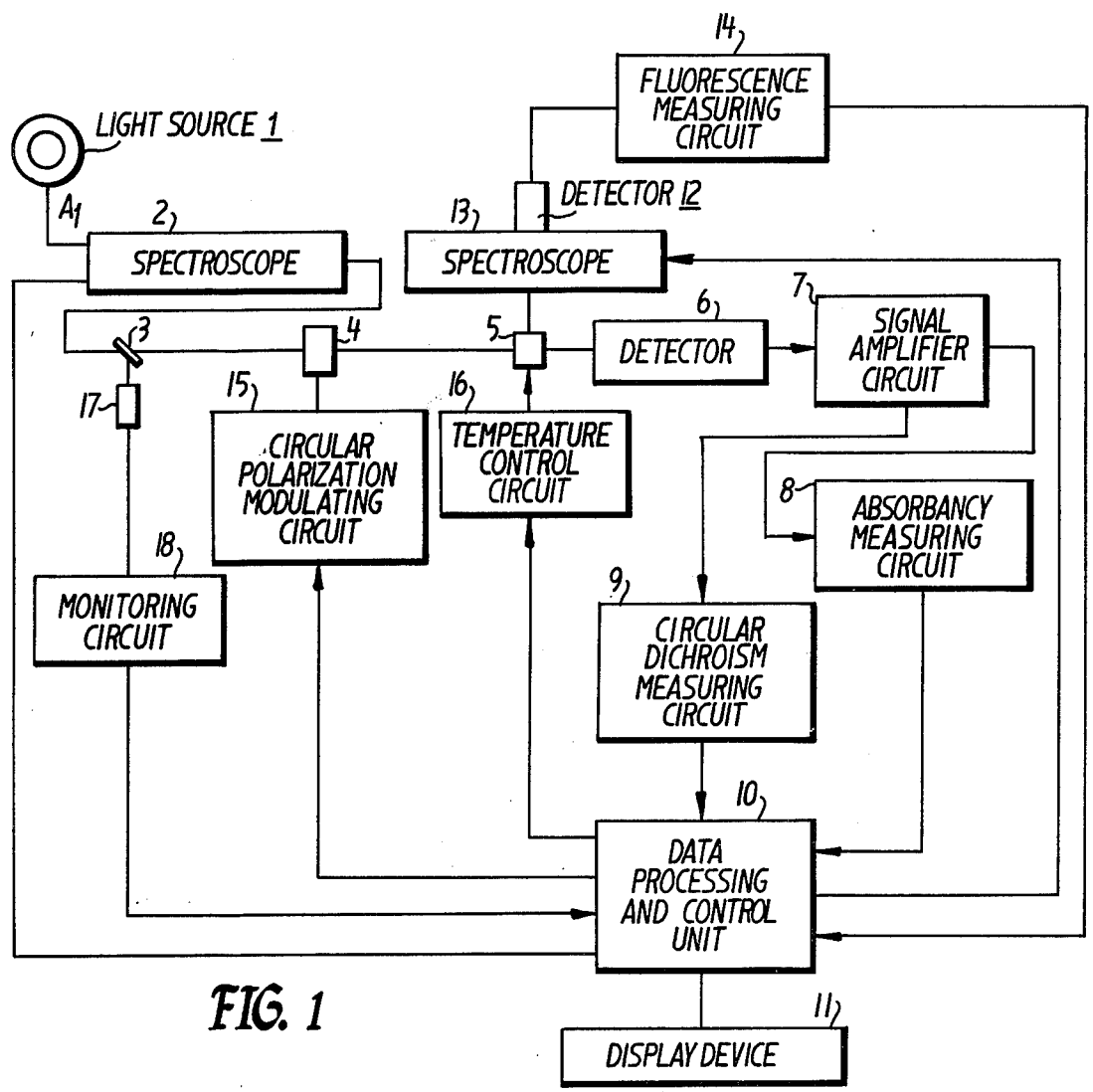
FIG. 1 is a block diagram of a preferred embodiment according to this invention.

FIG. 1 is a block diagram showing a preferred embodiment of this invention. Along a light axis $A_1$ from a light source 1 there are arranged a spectroscope 2, a beam splitter 3, a circular polarization modulator 4 consisting of a stress modulator and other elements, a sample cell 5 and a photoelectric detector 6 in sequence. As samples 4 are radiated by the circular polarizations, alternating left and right by a constant period because of the modulator 4, the photoelectric current output of detector 6, as a function of transmissions through said sample cell 5, contains both A.C. and D.C. components. Both components are fed to a signal amplifier circuit 7, and then amplified. Subsequently the D.C. component alone is fed to an absorbency measuring circuit 8, while the D.C. as well as A.C. components are fed to a circular dichroism measuring circuit 9. The respective outputs of the absorbency measuring circuit 8 and circular dichroism measuring circuit 9 are introduced into a data processing and control unit 10. This unit 10 performs operations of correction, correlation, generality and others. A display and record unit 11 consists of a graphic recorder, x-y plotter, teletypewriter or the like for indication of the arithmetic results.

As shown, detector 6, for the measurement of absorbency and circular dichroism, is disposed at the terminal end of the light axis $A_1$. According to this invention, another detector 12 is disposed by way of another spectroscope 13 along an extension axis $A_2$ crossed with light $A_1$ at the sample cell 5. This detector 12 detects fluorescence, i.e. photoenergy which said samples are excited by radiations to generate and to emit. The fluorescent output signal is fed to a measuring circuit 14, and then is introduced into the data processing and control unit 10 in the same manner as the other measured data.

The data processing and control unit 10 not only performs correlation and correction of the output data at the respective measuring circuits 8, 9, and 14, but also controls the spectroscope 13 for wavelength scanning of radiations to sample cell 5, the circular polarization modulator 4, and the temperature, pH value, concentration and other features of said sample cell. For these purposes, a circular polarization modulating circuit 15 and temperature control circuit 16 are provided respectively to receive instructions from the data processing and control unit 10 and respectively to control operations of circular polarization modulator 4 and the temperature and other conditions of said sample cell 5.

The strength of radiations to samples 5 is watched both by a photoelectric detector 17 which receives reflections from the beam splitter 3 and a monitoring circuit 18 including an amplifier of the so detected output. The so watched output is introduced into the data processing and control unit 10, where influences due to variations of radiations in accordance with their delay or wavelength can be adjusted by various measured data.

Since this invention is constituted as in the foregoing, it is possible to simultaneously measure the absorption (spectrum), circular polarization dichroism (spectrum) and fluorescence of given samples as parameters of their temperature, solution pH value, concentration and others.

In operation, when the data processing and control unit 10 is driven, the light source 1 is lit, and spectroscope 2 scans wavelengths, or selects predetermined wavelengths. The circular polarization modulating circuit 15 generates alternating electrical voltages with a constant period which it applies to the modulator 4, so that modulator 4 produces left and right alternating circular polarizations in accordance with said period. The modulator 4, which is composed of a stress modulator, is provided with piezo-electric crystallines and quartz glass or other optical crystal elements attached thereto. When alternating voltage is applied to said piezo-electrical crystallines, stresses are alternately produced in said optical elements and incident polarizations turn out left and right alternating circular polarizations due to the double refraction of said stresses. The modulator 4 could also have linear polarized elements inserted at the forward portion. The alternating circular polarizations with a constant period include a constant component and oscillatory component in accordance with said period. Transmissions through the sample cell 5 also include both components. It is to be noted that the D.C. component, corresponding to the constant component, from the detector 6 indicates the absorbency in accordance with the strength of radiations through the samples, and the A.C. component demonstrates the circular dichroism by showing a proportion to the D.C. component (aiming to the cancellation of proportional constants). The absorbency measuring circuit 8 takes out the D.C. component from the output of the amplifier 7 after amplification of the output of the detector 6, and the data processing and control unit 10 arithmetically works out values of the absorbency.

The circular dichroism measuring circuit 9 receives both the A.C. and D.C. currents. Thereafter, absorbency and circular dichroism indicating signals are produced by getting said A.C. current rectified then smoothened and by calculating its proportion to said D.C. current given.

It is evident likewise as in the case of the aforesaid absorbency that the detector 12 disposed at the terminal end of light axis $A_2$ through samples 5 is capable of detecting fluorescent luminescence by means of the spectroscope 13.

As the result, data concerning the absorbency, circular dichroism and fluorescence of given samples are simultaneously introduced into the data processing and control unit 10, where data concerning the strength of radiations are also supplied from the monitoring circuit 18. The data processing and control unit 10 performs digital operations for memorizing or recording individually respective data and watch data concerning radiation strength and further operations for efficient display of changes in time and of correlations among respective data. The contents of the latter processing operations are as follows:

(a) to obtain respective three dimensional spectra representing changes in time (parameter) of respective two dimensional data of an absorption spectrum, a circular dichroism spectrum and a fluorescence spectrum;

(b) to obtain respective three dimensional spectra representing changes in accordance with sample-solution concentration and pH value (parameter) of the respective two dimensional spectra;

(c) to obtain respective three dimensional spectra representing changes in sample temperature (parameter) of the respective two dimensional spectra;

(d) to obtain respective correlative diagrams of absorbency-circular dichroism, absorbency-fluorescent strength and fluorescent strength-circular dichroism as reference to sample temperature, concentration (pH), time and wavelength;

(e) to obtain three dimensional correlative diagrams by the same method as d), with x, y and z axes respectively to show absorbency, circular dichroism and fluorescent strength;

(f) to form correlation spectra by use of other parameters than said reference variables from the correlative diagrams of d) and c).

Processing operations for obtaining two or three dimensional data from primary data are itemized as aforesaid. These higher dimensional data provide useful information to represent the characteristics of biological samples in many side respects and also are helpful in detecting affected parts and the effects of clinical treatment.

As an important matter, this invention is to provide a simultaneous photometering system for multi-dimensional measurements, thereby useful data processing operation can be realized.

Figure 3:
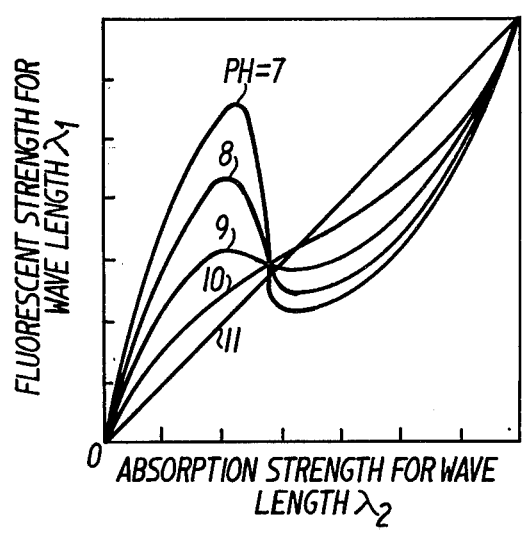
FIG. 3 is a correlative graph of fluorescent strength-absorbency strength as referenced to temperature and/or the parameter of pH values; and, FIG. 4 is a three dimensional correlative diagram showing absorbency-fluorescence-circular dichroism.
Figure 2:
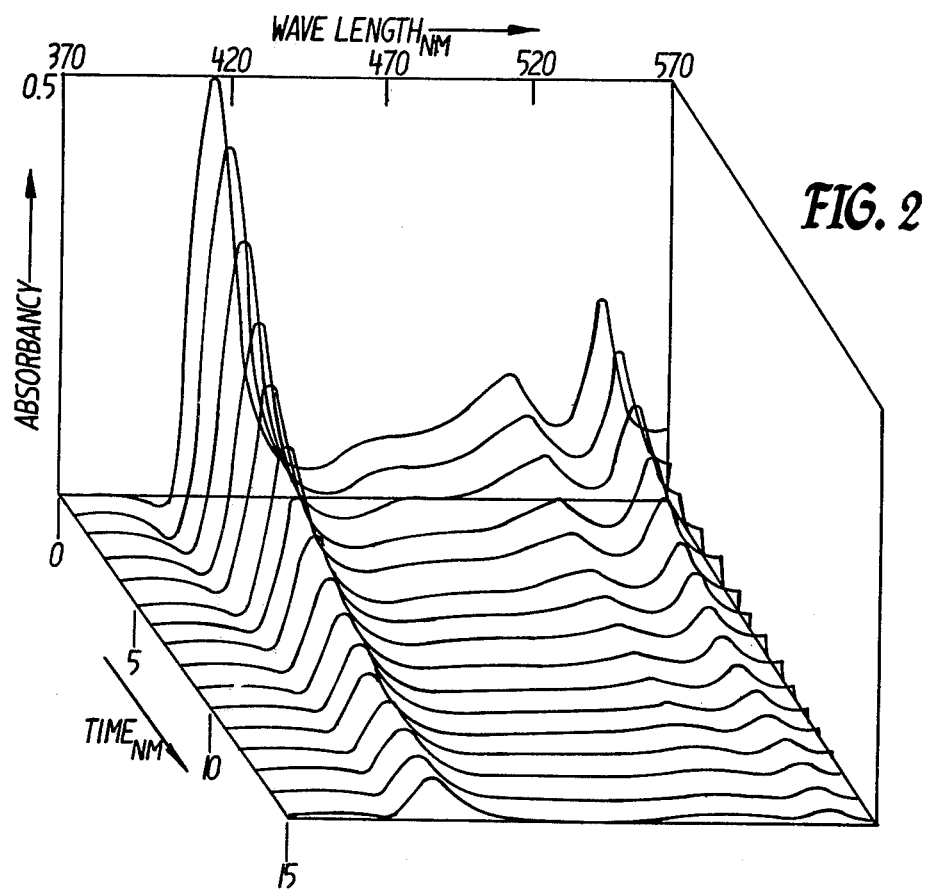
FIG. 2 is a three dimensional graph indicating changes in time of absorbency spectra of given samples.
Figure 4:
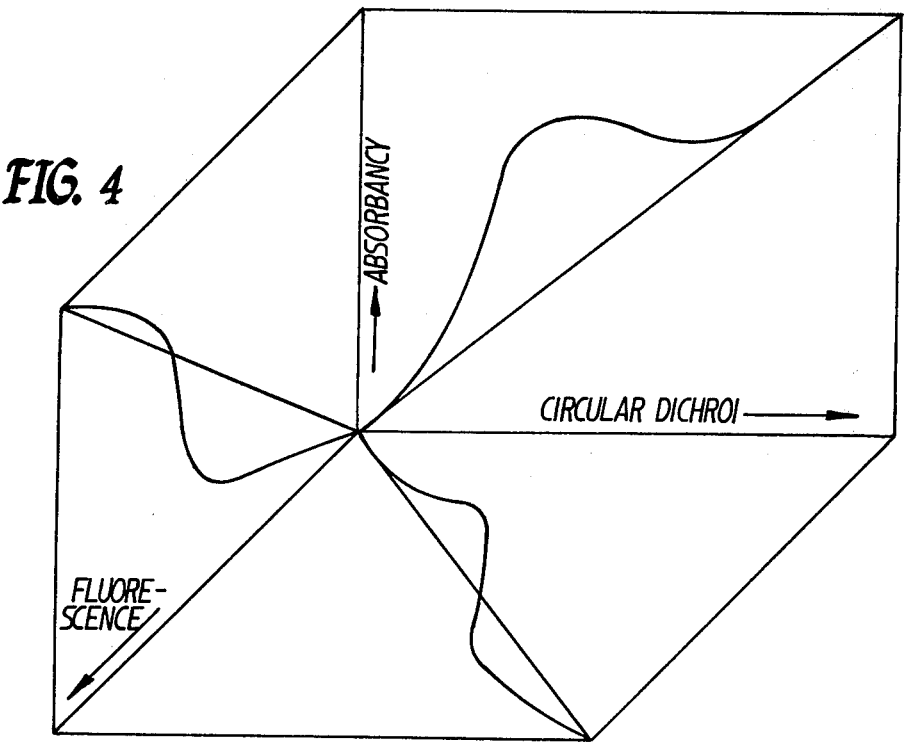

FIGS. 2 to 4 show graphic examples obtained by data processing operations according to this invention. FIG. 2 is a three dimensional plot measured over a period of time showing the changes in a spectrum of absorbency concerning cytochrome of oxidation and reduction types. This relation of oxidation and reduction speeds to spectrum change is well known. FIG. 3 is an expected correlative curve diagram of absorbency (wavelength $\lambda_2$) and fluorescent strength (wavelength $\lambda_1$) as referenced to temperature and parameters of pH values concerning given samples, from which changes in structure, stability and others in accordance with circumstances (pH and others) of said samples (biological materials) are known. FIG. 4 is a diagram showing the three dimensional correlative features of the aforesaid e) as variables of pH values for example. Besides, it is possible to obtain other graphic diagrams than ones of FIGS. 2 to 4, represented in aforesaid items a) to f) and selected according to given samples and purposes of measurement.

I claim:

1. A simultaneous photometering method for multi-dimensional measurements concerning biologically related materials, which comprises the steps of: radiating periodically left and right alternating circular polarizations of selected wavelength lights onto given samples; detecting the transmissions through said samples and measuring the circular dichroism and absorbency at a time; simultaneously detecting the strength of fluorescence emitted from said samples radiated; and displaying and recording said circular dichroism, absorbency and fluorescent strength in correlative manners.

2. A simultaneous photometering assembly for multi-dimensional measurements concerning biologically related material samples, which comprises: a light source for radiating light; a spectroscope for taking predetermined wavelengths out of said light; a modulator of said predetermined wavelength light into circular polarizations periodically alternating left and right for radiating said modulated light onto said sample; a photoelectric detector for measuring circular polarizations transmitted through said samples; a circuit means for taking absorbency signals out of the D.C. component from an output of said detector, said component representing the wavelength absorbency of said samples; another circuit means for detecting a ratio of the A.C. component to the D.C. component from said output and thereby measuring the circular dichroism signals of said samples; a spectroscope and detector assembly for detecting fluorescences emitted perpendicular to the modulated light axis from said samples; and still another circuit means measuring fluorescent luminescences of said samples from the output of said detector assembly.

3. The assembly according to claim 2, comprising means for automatically controlling the temperature of said samples.